United States Patent

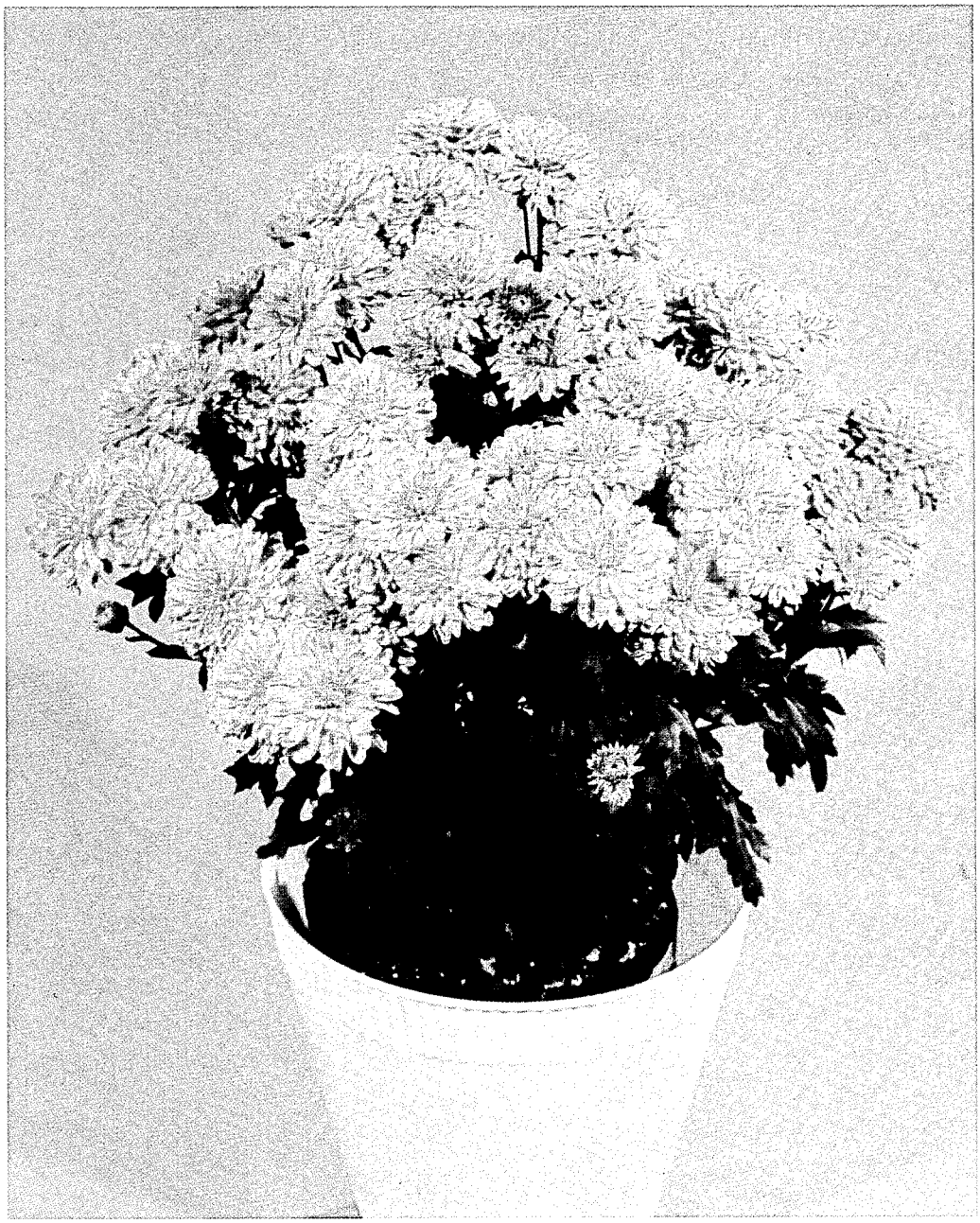

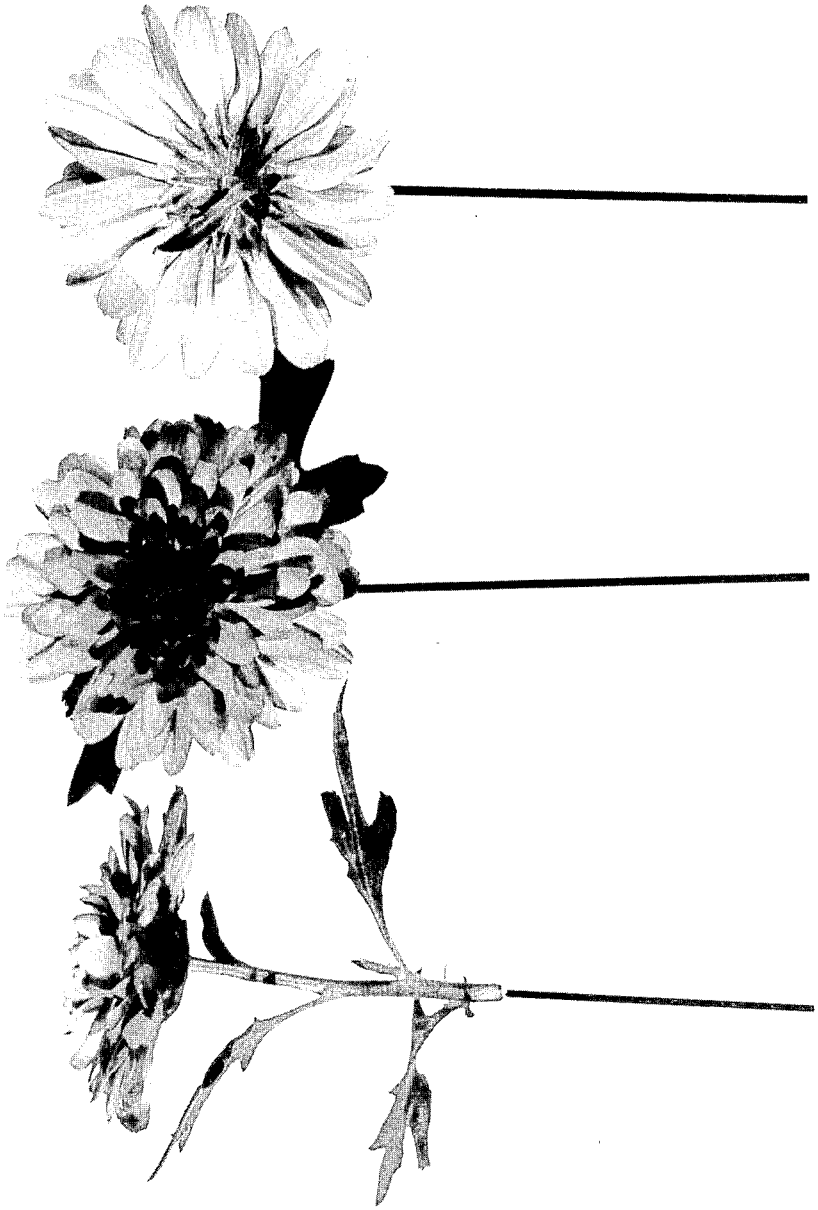

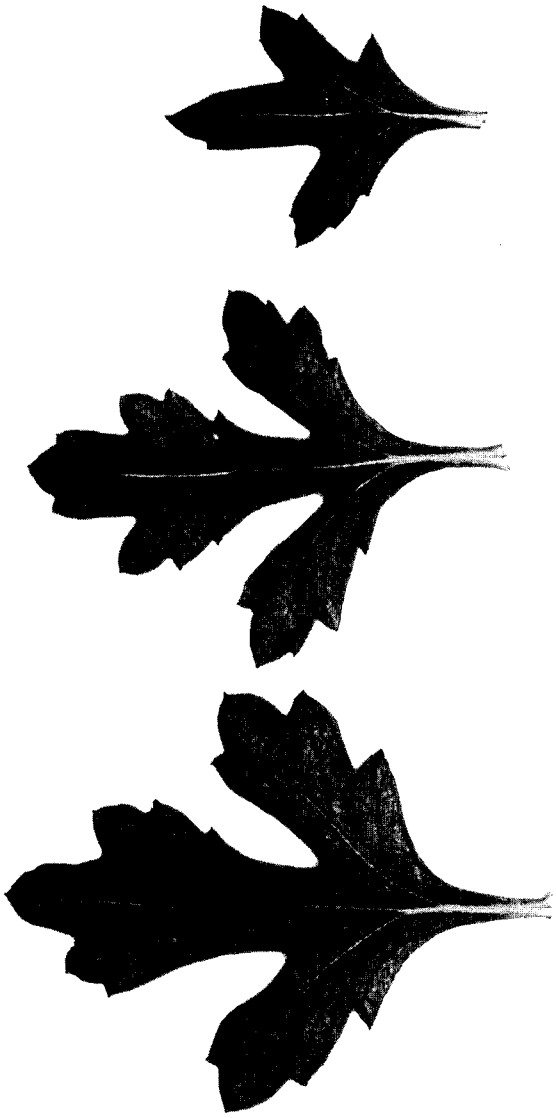

Plant Pat. 3,896

Patented June 1, 1976

3,896

CHRYSANTHEMUM PLANT

Walter H. Jessel, Jr., Doylestown, and William Erwin Duffett, Akron, Ohio, assignors to Yoder Brothers, Inc., Barberton, Ohio Filed Apr. 16, 1975, Ser. No. 568,570

Int. Cl. A01h 5/00

U.S. Cl. Plt.—75 1 Claim

The present invention comprises a new and distinct cultivar of *Chrysanthemum morifolium*, Ramat., hereinafter referred to by the cultivar name Ironsides (#73288015).

Ironsides was originated from a cross made in a controlled breeding program in Barberton, Ohio in the year 1972.

The female, or seed parent, was #72054029 (unnamed seedling), a bronze decorative originated by the present inventors from a cross between Festive Cushion (#66004001; unpatented; commercially available) and Minnautumn (#21620E07; unpatented, commercially available).

The male, or pollen parent, was #72037009 (unnamed seedling) a bronze pompon originated by the present inventors from a cross between #70023002 (unnamed seedling) and Minnautumn (#21620E07; unpatented; commercially available).

Ironsides was discovered and selected as a flowering seedling within the progeny of the stated cross by William E. Duffett and Walter H. Jessel, Jr. on May 2, 1973 in a controlled environment in Barberton, Ohio.

Ironsides is a product of a planned breeding program which had the objective of creating durable bronze decoratives for outdoor natural season field culture with early response, compact and spreading growth habit, and prolific flowering traits.

The first act of asexual reproduction of Ironsides was accomplished when vegetative cuttings were taken from the initial selection in July 1973 in a controlled environment in Barberton, by William E. Duffett and Walter H. Jessel, Jr. Horticultural examination of selected units initiated Oct. 23, 1973 has demonstrated that the combination of characteristics as herein disclosed for Ironsides are firmly fixed and are retained through successive generations of asexual reproduction.

Ironsides has not been observed under all possible environments. The phenotype may vary significantly with variations in environment such as temperature, light intensity, and daylength. The following observations, measurements, and comparisons describe plants grown in a field in Barberton, Ohio under outdoor environmental conditions which are generally described in Local Climatological Data, Annual Summary with Comparative Data, Akron, Ohio, U.S. Department of Commerce, National Oceanic and Atmospheric Administration, Environmental Data Service, Washington, D.C. 1972, 1973, 1974 and Table of Sunrise, Sunset and Twilight, Supplement to the American Emphemeris, 1946, U.S. Naval Observatory, Washington, D.C., pg. 103.

The following traits have been repeatedly observed and are determined to be basic characteristics of Ironsides which in combination distinguish this chrysanthemum as a new and distinct cultivar:

(1) Orange bronze inflorescence color.
(2) Flat inflorescence form.
(3) Decorative inflorescence type.
(4) Diameter across face of inflorescence up to 2.25 inches at maturity.
(5) Medium plant height.
(6) Compact, semi-upright general appearance of plant.
(7) Average natural season flowering date of September 22.
(8) Average controlled flowering response period of 6 weeks.

The accompanying photographic drawings show typical inflorescence and foliage characteristics of Ironsides, with colors being as nearly true as possible with illustrations of this type. Sheet 1 is a color photograph of Ironsides. Sheet 2 comprises a black and white photograph showing three different views of the inflorescence of Ironsides, and Sheet 3 is a black and white photograph showing the foliage of Ironsides at three stages of growth.

Of the many comercial cultivars known to the present inventors, the most similar existing cultivar in comparison to Ironsides is Flaming Sun (#21700E07; unpatented). Reference is made to attached Chart A which compares certain characteristics of Flaming Sun with the same characteristics of Ironsides.

In comparison in general terms to Flaming Sun, Ironsides has an earlier natural season flowering date, smaller diameter across face of influorescence, taller height, more bronze inflorescence color, and shorter controlled flowering response period.

In the following description, color references are to The Munsell Limit Color Cascade, 1972 edition. The color values were determined between 10:30 a.m. and 11:00 a.m. on Jan. 14, 1975 under 190 foot candle light intensities, at Barberton, Ohio.

Botanical Classification: *Chrysanthemum morifolium*, Ramat., cv Ironsides.

I. INFLORESCENCE

A. Capitulum:
*Form.*—Flat.
*Type.*—Decorative.
*Permanence.*—14–16 days.
*Diameter across face.*—2 inches.

B. Corolla of ray florets:
*Texture (adaxial).*—Glabrous.
*Appearance and form.*—Ligulate.
*Arrangement.*—Whorled on receptacle.
*Persistence.*—Resists shatter.
*Color (abaxial).*—31–9 to 31–13.
*Color (adaxial).*—29–4 with more orange.

C. Reproductive Organs:
*Androecium.*—Present disc florets only, syngenesious stamen; scant pollen.
*Gynoecium.*—Present both ray and disc florets; inferior, bicarpellate ovary; single style; 2-lobed stigma.

II. PLANT

A. General appearance: Medium height; semi-upright.
B. Duration and texture: Perennial; herbaceous.
C. Foliage:
*Color (abaxial).*—21–15 to 21–24.
*Color (adaxial).*—21–13 overlaid with white.
*Shape.*—Spatulate; deeply lobed.
*Texture.*—Glabrous.
*Arrangement.*—Alternate.
*Veination.*—Prominent.
*Margin.*—Deeply serrated.

We claim:

1. A new and distinct cultivar of chrysanthemum plant characterized as to uniqueness by the combined characteristics of orange bronze inflorescence color, flat inflorescence form, decorative inflorescence type, up to 2.25 inches diameter across face of inflorescence at maturity, medium plant height, compact, semi-upright general appearance of plant, average natural season flowering date of September 22, and its average controlled flowering response period of 6 weeks.

CHART A—COMPARISON OF IRONSIDES AND FLAMING SUN

| Cultivar | Natural season flower date | Diameter across face of inflorescence, inches | Inflorescence form and type | Plant height | Branching habit | Inflorescence color | Controlled flowering response period |
|---|---|---|---|---|---|---|---|
| Ironsides | Sept. 22 | 1¾–2¼ | Flat, decorative | Medium | Semi-upright | Orange bronze | 6 weeks. |
| Flaming Sun | Oct. 4 | 2¼–2¾ | do | Short | do | Orange | 7 weeks. |

NOTE.—Comparisons made of plants grown under natural season outdoor field conditions in Barberton, Ohio.

No references cited.

ROBERT E. BAGWILL, Primary Examiner